(12) United States Patent
Simhambhatla et al.

(10) Patent No.: US 7,794,743 B2
(45) Date of Patent: *Sep. 14, 2010

(54) POLYCATIONIC PEPTIDE COATINGS AND METHODS OF MAKING THE SAME

(75) Inventors: Murthy V. Simhambhatla, Sunnyvale, CA (US); Ni Ding, San Jose, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1412 days.

This patent is subject to a terminal disclaimer.

(21) Appl. No.: 11/218,654

(22) Filed: Sep. 2, 2005

(65) Prior Publication Data

US 2006/0062821 A1    Mar. 23, 2006

Related U.S. Application Data

(63) Continuation-in-part of application No. 10/177,114, filed on Jun. 21, 2002, now Pat. No. 7,011,842.

(51) Int. Cl.
*A61F 2/04*    (2006.01)
*A61K 9/50*    (2006.01)

(52) U.S. Cl. ..................... 424/426; 424/499
(58) Field of Classification Search ............... None
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,835,175 A | 9/1974 | Carpino et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,908,404 A | 3/1990 | Benedict et al. |
| 4,917,309 A | 4/1990 | Zander et al. |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,025,001 A | 6/1991 | Loscalzo et al. |
| 5,100,992 A | 3/1992 | Cohn et al. |
| 5,112,457 A | 5/1992 | Marchant |
| 5,133,742 A | 7/1992 | Pinchuk |
| 5,155,137 A | 10/1992 | Keefer et al. |
| 5,163,952 A | 11/1992 | Froix |
| 5,165,919 A | 11/1992 | Sasaki et al. |
| 5,187,183 A | 2/1993 | Loscalzo et al. |
| 5,202,129 A | 4/1993 | Samejima et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,356,890 A | 10/1994 | Loscalzo et al. |
| 5,366,997 A | 11/1994 | Keefer et al. |
| 5,380,299 A | 1/1995 | Fearnot et al. |
| 5,405,919 A | 4/1995 | Keefer et al. |
| 5,417,981 A | 5/1995 | Endo et al. |
| 5,424,077 A | 6/1995 | Lajoie |
| 5,428,070 A | 6/1995 | Cooke et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |

(Continued)

FOREIGN PATENT DOCUMENTS

DE     42 24 401     1/1994

(Continued)

OTHER PUBLICATIONS

Anonymous, Reducing the pH of a peptide oligomer to prepare for systemic delivery, Defensive Publication, Research Disclosure, p. 905 (Aug. 2003).

(Continued)

*Primary Examiner*—Carlos A Azpuru
(74) *Attorney, Agent, or Firm*—Squire, Sanders & Dempsey L.L.P.

(57) ABSTRACT

Polycationic peptide coatings for implantable medical devices and methods of making the same are described. The methods include applying an emulsion on the device, the emulsion including a polymer and a polycationic peptide. Other methods include incorporation of the polycationic peptide in microspheres and liposomes.

29 Claims, No Drawings

U.S. PATENT DOCUMENTS

| | | |
|---|---|---|
| 5,482,720 A | 1/1996 | Murphy et al. |
| 5,485,496 A | 1/1996 | Lee et al. |
| 5,516,881 A | 5/1996 | Lee et al. |
| 5,536,723 A | 7/1996 | Loscalzo et al. |
| 5,543,099 A | 8/1996 | Zhang et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,639,441 A | 6/1997 | Sievers et al. |
| 5,644,020 A | 7/1997 | Timmermann et al. |
| 5,649,977 A | 7/1997 | Campbell |
| 5,650,442 A | 7/1997 | Mitchell et al. |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,804,318 A | 9/1998 | Pinchuk et al. |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,852,058 A | 12/1998 | Cooke et al. |
| 5,854,376 A | 12/1998 | Higashi |
| 5,858,746 A | 1/1999 | Hubbell et al. |
| 5,861,168 A | 1/1999 | Cooke et al. |
| 5,865,814 A | 2/1999 | Tuch |
| 5,869,127 A | 2/1999 | Zhong |
| 5,873,904 A | 2/1999 | Ragheb et al. |
| 5,874,165 A | 2/1999 | Drumheller |
| 5,876,433 A | 3/1999 | Lunn |
| 5,877,224 A | 3/1999 | Brocchini et al. |
| 5,879,713 A | 3/1999 | Roth et al. |
| 5,891,459 A | 4/1999 | Cooke et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,945,452 A | 8/1999 | Cooke et al. |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,060,534 A | 5/2000 | Ronan et al. |
| 6,063,432 A | 5/2000 | Maxwell et al. |
| 6,077,543 A | 6/2000 | Gordon et al. |
| 6,080,488 A | 6/2000 | Hostettler et al. |
| 6,095,134 A | 8/2000 | Sievers et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,117,872 A | 9/2000 | Maxwell et al. |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,183,783 B1 | 2/2001 | Benoit et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,228,346 B1 | 5/2001 | Zhang et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,166 B1 | 10/2001 | Barry et al. |
| 6,306,176 B1 | 10/2001 | Whitbourne |
| 6,306,993 B1 | 10/2001 | Rothbard et al. |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |

| | | |
|---|---|---|
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossaony et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,481 B1 | 6/2004 | Larik et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |

| | | |
|---|---|---|
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Anderson et al., *Nitric-Oxide and Nitrovasodilators: Similarities, Differences and Potential Interactions*, JACC 24(2):555-566 (1994).

Anderson et al., *Close Relation of Endothelial Function in the Human Coronary and Peripheral Circulations*, JACC 26(5):1235-1241 (1995).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Bode-Boger et al., *Elevated L-Arginine/Dimethylarginine Ratio Contributes to Enhanced Systemic NO Production by Dietary L-Arginine in Hypercholesterolemic Rabbits*, Biochem. And Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):I-32(1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vasc. Biol. 16(1):44-50 (1996).

Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis*, Adv. Vasc. Path. 1150:3-14 (1997).

Cooke, *Does ADMA Cause Endothelial Dysfunction?*, Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis an Arginine Deficiency Disease?*, J. Investi. Med. 46(8):377-380 (1998).

Cooke, *Nutriceuticals for Cardiovascular Health*, Am. J. Cardio., 82(10A):43S-46S (1998).

Cooke, *Role of Nitric Oxide in Progression and Regression of Atherosclerosis*, West. J. Med. 164(5):419-424 (1996).

Cooke, *The 1998 Nobel Prize in Medicine: Clinical Implications for 1999 and Beyond*, Vasc. Med. 4:57-60 (1999).

Cooke, *The Endothelium: A New Target for Therapy*, Vasc. Med. 5:49-43 (2000).

Cooke, *The Pathophysiology Of Peripheral Arterial Disease: Rational Targets for Drug Intervention*, Vasc. Med. 2:227-230 (1997).

Creager et al., *L-Arginine Improves Endothelium-Dependent Vasodilation in Hypercholesterolemic Humans*, J. Clin. Investi. 90:1248-1253 (1992).

Drexler et al., *Effect of L-Arginine on Coronary Endothelial Function in Cardiac Transplant Recipients: Relation to Vessel Wall Morphology*, Circ. 89(4):1615-1623 (1994).

Drexler et al., *Endothelial Dysfunction in the Coronary Circulation After Cardiac Transplantation: Effect of L-Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

http://www.lf2.cuni.dz/physiolres/1997/issue5/iss5cl6.html,

Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).

Gaiser et al., *Lethal Short-Limbed Dwarfism in Transgenic Mice with an Arginine to Cysteine Substitution in AIpha-I (II) Procollagen* (Abstract 3369), Mol. Biol. Cell 7:579A (1996).

Ganz et al., *Coronary Vasospasm in Humans—The Role of Atherosclerosis and of Impaired Endothelial Vasodilator Function*, Basic Res. Cardiol. 86(Suppl 2):215-222 (1991).

Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1996).

Gregory et al., *Nitric Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).

Helmus, *Overview of Biomedical Materials*, MRS Bulletin, pp. 33-38 (Sep. 1991).

Heeschen et al., *Hypercholesterolemia Impairs Angiogenic Response to Hind Limb Ischemia: Role of ADMA* (Abstract 2490), Circ. I-473 (1999).

Herdeg et al., *Antiproliferative Stent Coatings: Taxol and Related Compounds*, Semin. Intervent. Cardiol. 3:197-199 (1998).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).

Huang et al., *Biodegradable Polymers Derived from Aminoacids*, Macromol. Symp. 144, 7-32 (1999).

Huet et al., *Structural Homologies Between Two HLA B27-Restricted Peptides Suggest Residues Important for Interaction with HLA B27*, Intl. Immunol. 2(4):311-316 (1990).

Hutchison et al., *Effects of L-Arginine on Atherogenesis and Endothelial Dysfunction Due to Secondhand Smoke*, Hyperten. 34:44-50 (1999).

Inoue et al., *An AB block copolymer of oligo(methyl methacrylate) and poly(acrylic acid) for micellar delivery of hydrophobic drugs*, Journal of Controlled Release 51:221-229 (1998).

Jang et al., *Angiogenesis is Impaired by Hypercholesterolemia: Role of Asymmetric Dimethylarginine*, Circ. 102:1414-1419 (2000).

Jang et al., *L-Arginine Reverses the Anti-Angiogenic Effects of Asymmetric Dimethylarginine* (Abstract), J. Investi. Med. 4(2):86A (1999).

Jozkowicz et al., *Genetic Augmentation of Nitric Oxide Synthase Increases the Vascular Generation of VEGF*, Cardiovasc. Res. 51:773-783 (2001).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha,\omega$-Alkylene Diesters, and Aliphatic Dicarbolic Acids*, Journal of Polymer Science, Part A: Polymer Chemistry, 37(4), 391-407 (1999).

Kown et al., *Arginine Polymers Inhibit Graft Coronary Artery Disease Following Cardiac Transplantation* (Abstract 726), Transplant. 69(8):S300 (2000).

Kown et al., *L-Arginine Polymers Inhibit the Development of Vein Graft Neointimal Hyperplasia*, J. Thorac. Cardiovasc. Surg. 121(5):971-980 (2001).

Kown et al., *L-Arginine Polymer Mediated Inhibition of Graft Coronary Artery Disease After Cardiac Transplantation*, Transplant. 71(11):1542-1548 (2001).

Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).

Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).

Kyte et al., *A Simple Method for Displaying the Hydropathic Character of a Protein*, J. Mol. Biol. 157:105-132 (1982).

Latron et al., *Positioning of a Peptide in the Cleft of HLA-A2 by Complementing Amino Acid Changes*, PNAS 88:11325-11329 (1991).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Lieberman et al., *Estrogen Improves Endothelium-Dependent, Flow-Mediated Vasodilation in Postmenopausal Women*, Annals Intern. Med. 121(12):936-941 (1994).

Lieberman et al., *Flow-Induced Vasodilation of the Human Brachial Artery is Impaired in Patients <40 Years of Age with Coronary Artery Disease*, Am. J. Cardiol. 78:1210-1214 (1996).

Lim et al., *Acute Local Delivery of L-Arginine Reduces Long Term Intimal Thickening and Macrophage Infiltration* (Abstract 2346), Circ. 94(8):I403 (1996).

Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).

Lissin et al., *Maintaining the Endothelium: Preventive Strategies for Vessel Integrity*, Prev. Cardio. 3:172-177 (2000).

Liu et al., *Drug release characteristics of unimolecular polymeric micelles*, Journal of Controlled Release 68:167-174 (2000).

Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).

Maxwell et al., *A Nutritional Product Designed to Enhance Nitric Oxide Activity Restores Endothelium-Dependent Function in Hypercholesterolemia*, J. Investi. Med. 47(2):45A (1999).

Maxwell et al., *Cardiovascular Effects of L-Arginine,* Curr. Opin. Nephrol. Hyperten. 7:63-70 (1998).

Maxwell et al., *Endothelial Dysfunction in Hypercholesterolemia is Reversed by a Nutritional Product Designed to Enhance Nitric Oxide Activity,* Cardiovasc. Drugs Therapy 14:309-316 (2000).

Maxwell et al., *Improvement in Walking Distance and Quality of Life in Peripheral Arterial Disease by a Medical Food* (Abstract 86), Nitric Oxide: Biology and Chemistry, 4(3):232 (2000).

Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercise Capacity in Association with Augmented Nitric Oxide Production,* J. Appl. Physiol. 90:933-938 (2001).

Maxwell et al., *Limb Blood Flow During Exercise is Dependent on Nitric Oxide,* Circ. 98:369-374 (1998).

Maxwell et al., *Modulation of the Nitric Oxide Synthase Pathway in Atherosclerosis,* Exp. Physiol. 83:573-584 (1998).

Maxwell et al., *Nutritional Therapy for Peripheral Arterial Disease: A Double-Blind, Placebo-Controlled, Randomized Trial of HeartBar®,* Vasc. Med. 5:11-19 (2000).

Maxwell et al., *The Role of Nitric Oxide in Atherosclerosis,* Cor. Art. Dis. 10:277-286 (1999).

Marconi et al., *Covalent bonding of heparin to a vinyl copolymer for biomedical applications,* Biomaterials 18(12):885-890 (1997).

Matsumaru et al., *Embolic Materials For Endovascular Treatment of Cerebral Lesions,* J. Biomater. Sci. Polymer Edn 8(7):555-569 (1997).

Meredith et al., *Role of Endothelium in Ischemic Coronary Syndromes,* Am. J. Cardiol. 72(8):27C-32C (1993).

Meredith et al., *Role of Impaired Endothelium-Dependent Vasodilation in Ischemic Manifestations of Coronary Artery Disease,* Circ. 87(5) Suppl:V56-V66 (1993).

Mitchell et al.; *Polyarginine Enters Cells More Efficiently than Other Polycationic Homopolymers,* J. Peptide Res. 56:318-325 (2000).

Miyazaki et al., *Endogenous Nitric Oxide Synthase Inhibitor: A Novel Marker of Atherosclerosis,* Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate In The Absence Of Changes In Arterial Blood Pressure When Applied Topically To The Sino-Atrial Node In The Anaesthetized Pig,* J. Physiol. (2000), printed Jun. 12, 2001.

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice,* Chem. Pharm. Bull. 33(6) 2490-2498 (1985).

Miyazawa et al., *Effects of Pemirolast and Tranilast on Intimal Thickening After Arterial Injury in the Rat,* J. Cardiovasc. Pharmacol., pp. 157-162 (1997).

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study,* Lancet 353:1838-1842 (1999).

Niebauer et al., *Gene Transfer of Nitric Oxide Synthase: Effects on Endothelial Biology,* JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis,* Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Nordrehaug et al., *A novel biocompatible coating applied to coronary stents,* EPO Heart Journal 14, p. 321 (P1694), Abstr. Suppl. (1993).

Ohno et al., *Shear Stress Elevates Endothelial cGMP: Role of a Potassium Channel and G Protein Coupling,* Circ. 88:193-197 (1993).

Ohsawa et al., *Preventive Effects of an Antiallergic Drug, Pemirolast Potassium, on Restenosis After Percutaneous Transluminal Coronary Angioplasty,* American Heart Journal 136(6):1081-1087 (Dec. 1998).

Ozaki et al., *New Stent Technologies,* Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin,* Bioconjucate Chemistry 11(2):131-139 (Mar./Apr. 2000).

Peng et al., *Role of polymers in improving the results of stenting in coronary arteries,* Biomaterials 17:685-694 (1996).

Raby et al., *Changing Vasomotor Responses of Coronary Arteries to Nifedipine,* Am. Heart J. 126(2):333-338 (1993).

Rothbard et al., *Conjugation of Arginine Oligomers to Cyclosporin A Facilitates Topical Delivery and Inhibition of Inflammation,* Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide,* Intl. Immunol. 1(4):487-495 (1989).

Saotome, et al., *Novel Enzymatically Degradable Polymers Comprising α-Amino Acid, 1,2-Ethanediol, and Adipic Acid,* Chemistry Letters, pp. 21-24, (1991).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain,* J. Exp. Med. 159:1351-1370 (1984).

Schwarzacher et al., *L-$N^G$-Nitro-Arginine Methyl Ester in the Anesthetized Rabbit: Venous Vasomotion and Plasma Levels,* J.Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone* in vivo *Using Intravascular Ultrasound,* J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity* in vivo, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty,* Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester,* Clin. Exp. Pharmacol. Physiol. 23(6/7):490-492.

Selwyn et al., *Pathophysiology of Ischemia in Patients with Coronary Artery Disease,* Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations,* Published Jul. 21, 1999, printed Feb. 19, 2002.

Shigeno, *Prevention of Cerebrovascular Spasm by Bosentan, Novel Endothelin Receptor*, Chemical Abstract 125:212-307 (1996).

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract I20), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl 1:1942 (1992).

Singer et al., *Dietary Supplements of L-Arginine Reduce Atherogenesis and Alter Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and The Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by The NO Precursor* (Abstract 765-4), JACC 25:276A (1995).

Todd et al., *Regulation of Loblolly Pine (Pinus taeda L.) Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion: in vivo Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase As an in vivo Gene Transfer Approach to Prevent Neointima Formation After Vascular Injury*, Clin. Res. 42(2):180A (1994).

van Beusekom et al., *Coronary stent coatings*, Coronary Artery Disease 5(7):590-596 (Jul. 1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wilensky et al., *Methods and Devices for Local Drug Delivery in Coronary and Peripheral Arteries*, Trends Cardiovasc. Med. 3(5):163-170 (1993).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Yokoyama et al., *Characterization of physical entrapment and chemical conjugation of adriamycin in polymeric micelles and their design for in vivo delivery to a solid tumor*, Journal of Controlled Release 50:79-92 (1998).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine In Cardiovascular Health*, U.S. Pharmacist Continuing Education, printed Sep. 12, 2002.

POLYCATIONIC PEPTIDE COATINGS AND METHODS OF MAKING THE SAME

CROSS REFERENCE

This application is a continuation-in-part of application Ser. No. 10/177,114, filed Jun. 21, 2002, now U.S. Pat. No. 7,011,842 which is hereby incorporated herein by reference.

BACKGROUND OF THE INVENTION

1. Field of the Invention

This invention relates to the field of implantable medical devices, such as stents. More particularly, this invention is directed to coatings for devices, the coatings including peptides such as polymers and/or oligomers of L-arginine.

2. Description of the Background

In the field of medical technology, there is frequently a necessity to administer a therapeutic substance locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results. For the treatment of vascular occlusions, such as restenosis, stents are being modified to administer therapeutic substances locally. One method of medicating a stent is with the use of a polymer coating impregnated with a therapeutic substance. The coating allows for the sustained release of the substance at the treatment site. L-arginine, or polypeptide oligomeric derivatives or analogs thereof, for example, those containing 5 to 20 amino acid units are one example of a therapeutic substance that can be used in conjunction with a stent.

L-arginine is a known precursor of endothelium derived nitric oxide (NO). NO is synthesized from L-arginine, or its polymeric and/or oligomeric derivatives, by the enzyme NO synthase oxygenase, a homodimeric flavo-hemoprotein that catalyzes the 5-electron oxidation of L-arginine to produce NO and L-citrulline. Among other therapeutic properties, NO regulates vascular tone, inhibits platelet aggregation, and inhibits vascular smooth muscle proliferation. These therapeutic properties are believed to contribute to the reduction or elimination of neo-intimal hyperplasia in vascular injury models.

U.S. Pat. No. 5,861,168 to Cooke et al. teaches that NO activity is reduced after vascular injury. Cooke et al. also teach that administering L-arginine as the NO precursor helps to restore vascular NO activity in patients with endothelial vasodilator dysfunction due to restenosis. It has been also taught that oligomeric peptides comprising 6 to 15 units of L- or D-arginine can be effective transfectors of cells (see, Mitchell, et al., *J. Peptide Res., vol.* 56, p. 318 (2000)) and, using a rabbit vein-graft model, it has been demonstrated that oligomers of L- or D-arginine can inhibit vascular smooth cell proliferation by efficiently transfecting cells. See, Uemura, et al., *Circulation, vol.* 102, p. 2629 (2000). Using the rabbit model, it has also been shown that intramural administration of L-arginine inhibits lesion formation in a hypercholesterolemic balloon injury. See, Schwarzacher et al. *Circulation*, vol. 95, p. 1863 (1997).

Accordingly, it is desirable to incorporate L-arginine, or its polymers and/or oligomers into a stent coating. The present application describes the methods that can be used to achieve this goal.

SUMMARY

The embodiments of the present invention generally encompass the field of medical devices, wherein the medical device can comprise a stent. More particularly, this invention is directed to coatings which include polycationic peptides such as polymers and/or oligomers of L-arginine such as, for example, hepta-arginine.

In some embodiments, the present invention includes an implantable medical device comprising a coating, wherein the coating includes a dispersed particle phase comprising a polycationic peptide. In these embodiments, the particle can comprise a microsphere or liposome.

In some embodiments, the invention includes a method of delivering an agent to a mammalian tissue, wherein the method comprises contacting the coatings of the present invention with mammalian tissue under in vivo conditions. In these embodiments, the tissue can comprise a vascular tissue.

In some embodiments, the invention includes a method of preventing or treating a disease comprising implanting the coatings of the present invention in a vascular lumen. In these embodiments, the disease can include a vascular disease comprising restenosis, vulnerable plaque, or a combination thereof, and the implanting can include the placement of a stent.

DETAILED DESCRIPTION

The compositions and methods of the present invention apply to the formation of medical devices and coatings. Next generation medical devices and coatings can be designed to target patients, for example, that may not respond as well to current medical devices and coatings. Accordingly, particular agents or a combination agent delivery may be more effective.

The medical devices and coatings can include layers having agents. In some embodiments, the medical device includes a stent, wherein the thickness of the struts that form the structure of the stent can be referred to as a layer or, in some embodiments, a combination of layers. In other embodiments, a layer or combination of layers can be applied as a coating on a surface of a medical device such as, for example, a stent. In other embodiments, the layers can be applied as a coating on select surfaces such as, for example, the abluminal surface of a stent. In other embodiments, the layers can be applied in predetermined geometrical patterns on select surfaces of a medical device such as, for example, a stent.

An "agent" can be a moiety that may be bioactive, biobeneficial, diagnostic, plasticizing, or have a combination of these characteristics. For example, an agent can be a drug. A "moiety" can be a functional group composed of at least 1 atom, a bonded residue in a macromolecule, an individual unit in a copolymer or an entire polymeric block. It is to be appreciated that any medical devices that can be improved through the teachings described herein are within the scope of the present invention.

In many embodiments, the agents can be dissolved in the polymeric matrix, exist in a dispersed phase within the polymeric matrix, or a combination thereof. In some embodiments, the agent component of a polymeric matrix can dissolve in a polymer phase and form a dispersed phase upon removal of the solvent used to form the composition. For example, an agent may be combined with a polymer matrix as a blend, a chemical conjugation, or a combination thereof, which affects the rate of release. The agent may also be sandwiched between polymer layers, encapsulated within a polymer network, or any combination thereof, thereby providing a desired agent concentration such as, for example, a desired spike in agent concentration at the boundary of a polymeric matrix.

L-arginine, also known as 2-amino-5-guanidinovaleric acid, can act as an agent and is an amino acid having a formula $NH=C(NH_2)-NH-CH_2-CH_2-CH_2-CH(NH_2)-COOH$. Polymers and/or oligomers of L-arginine that can be used are hereinafter referred to as "PArg" which comprise a plurality of repeating monomeric amino acid units connected with peptide bonds. PArg has a general formula $H[NH-CHX-CO]_p-OH$, where "p" can be within a range of 5 and 1,000, typically, within a range of between 6 and 20. For example, a heptamer (designated R7), having p=7, can be used. In the formula of PArg "X" is 1-guanidinopropyl radical having the structure $-CH_2-CH_2-CH_2-NH-C(NH_2)=NH$. The terms "polymers and/or oligomers of L-arginine," "poly-L-arginine," and "PArg" are intended to include L-arginine in both its polymeric and oligomeric form.

In addition to PArg, other polycationic peptides can be incorporated into the stent coatings. Examples of alternative polycationic peptides include mixtures of poly(L-arginine), poly(D-arginine), mixtures of poly(D-arginine), poly(L-lysine), poly(D-lysine), and poly(6-guanidino-α-aminobutyric acid). Those having ordinary skill in the art may choose to use other appropriate peptides if desired.

Forming Compositions

The compositions taught herein can be used in some embodiments to form medical articles such as, for example, medical devices, coatings, or a combination thereof. The medical articles can include a combination of agents, wherein each of the agents (i) can be incorporated in the device or coating without cross-contamination from the other agents; (ii) can perform its function substantially free from interference from the other agents, (ii) can be incorporated in the device or coating such that the agent has a predetermined release rate and absorption rate; and (iv) can be combined with other agents that are bioactive, biobeneficial, diagnostic, and/or control a physical property or a mechanical property of a medical device.

The terms "combine," "combined," "combining," and "combination" all refer to a relationship between components of a composition and include blends, mixtures, linkages, and combinations thereof, of components that form the compositions. The linkages can be connections that are physical, chemical, or a combination thereof.

Examples of physical connections include, but are not limited to, an interlinking of components that can occur, for example, in interpenetrating networks and chain entanglement. Examples of chemical connections include, but are not limited to, covalent and non-covalent bonds. Covalent bonds include, but are not limited to, simple covalent bonds and coordinate bonds. Non-covalent bonds include, but are not limited to, ionic bonds, and inter-molecular attractions such as, for example, hydrogen bonds and attractions created by induced and permanent dipole-dipole interactions. All of these types of combinations can have a variable effect on the measured diffusion coefficient.

The material considerations include, but are not limited to, the selection of the polymer and/or polymer combinations, the selection of the agent and/or agent combinations, the selection of the polymer/agent combinations, and the selection of the solvent and/or solvent combinations used to combine the materials for application. The scope of the present invention includes, but is not limited to, the following methods of forming compositions:

The compositions of the present invention include any combination of polymers, copolymers and agents. The compositions can include not only polymers but also polymers combined with ceramics and/or metals, which can also affect the relationship between the elements in the system. Examples of ceramics include, but are not limited to, hydroxyapatite, BIOGLASS®, and absorbable glass. Examples of metals include, but are not limited to magnesium, copper, titanium, and tantalum.

Polymeric matrices that are formed in the present invention should meet particular requirements with regard to physical, mechanical, chemical, and biological properties. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing.

An example of a chemical property that can affect performance of a biodegradable composition in vivo is the rate of absorption of the composition by a subject. An example of a biological property that can affect performance of a composition in vivo is the bioactive and/or biobeneficial nature of the composition in a subject, both of which are described below. The terms "subject" and "patient" can be used interchangeably and refer to an animal such as a mammal including, but not limited to, non-primates such as, for example, a cow, pig, horse, cat, dog, rat, and mouse; and primates such as, for example, a monkey or a human.

While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo. In some embodiments, an increase in hydrolysis can also increase the release rate of an agent by creating channels within a medical article or coating that can serve as transport pathways for diffusion of the agents from the composition within a subject.

The relative hydrophilicity of the components within a polymeric matrix affects the release of agents from a polymeric matrix, so control over the relative hydrophilicity of the components provides for control over the release rate of agents. Hydrophobicity and hydrophilicity, as used herein, are relative terms used to compare chemical moieties. The relative hydrophobicity and hydrophilicity of polymers, for example, can be determined by comparing the Hildebrand solubility parameter of each polymer, which is a value that is readily obtainable to one of skill in the art. In most embodiments, the "hydrophilic polymer" simply has a higher solubility parameter value than the "hydrophobic polymer." In embodiments containing more than two polymers, the polymers can be ranked in order by comparing their solubility parameters.

In some embodiments, water uptake can be increased by combining a hydrophilic moiety such as, for example, a hydrophilic polymer, with the polymeric matrix. In some embodiments, the hydrophilic polymers may also be non-fouling and include, but are not limited to, both biodegradable and non-biodegradable polymers such as, for example, poly(ethylene glycol)(PEG); poly(ethylene oxide); poly(ethylene glycol-co-propylene oxide)(PEG-PPO); dextran; dextrin; poly(vinyl alcohol); poly((2-hydroxyethyl)methacrylate) (HEMA); poly(vinyl pyrrolidone); (PVP); poly(butylene terephthalate-co-ethylene glycol)(PBT-PEG or POLYAC- TIVE™); poly(alkylene oxalates); pluronic acid; sulfonated polystyrene; block copolymers with a bioabsorbable block and a perfluoro chain; PEG-caprolactone; PEG-D,L-lactide; biomolecules such as fibrin, fibrinogen, cellulose, starch, collagen, heparin and hyaluronic acid; poly(vinyl alcohols); and combinations thereof.

In some embodiments, the hydrophilic moieties include, but are not limited to, poly(ethylene glycol) and glycosaminoglycans such as, for example, heparin and hyaluronic acid. In some embodiments, the hydrophilic moiety can be added in the range of from about 0.01% to about 99.99%; from about 0.1% to about 99.9%; from about 1% to about 99%; from about 3% to about 97%; from about 5% to about 95%; from about 7% to about 93%; from about 10% to about 90%; from about 15% to about 85%; from about 20% to about 80%; from about 25% to about 75%; from about 30% to about 70%; from about 40% to about 60%; about 50%; or any range therein, wherein the percent is a weight percent based on total polymer in the composition. It is to be appreciated that in some embodiments, any one or any combination of the hydrophilic, non-fouling polymers taught herein could excluded from any embodiment taught herein for reasons known to one of skill in the art.

Without intending to be bound by any theory or mechanism of action, the tendency of hydrophilic polymers to leach out of the polymeric matrices of the present invention can be minimized by choosing a hydrophilic, non-fouling polymer having a molecular weight that is high enough to prevent or inhibit leaching. The choice of molecular weight can be based on the hydrophilicity of the polymer—the more hydrophilic the polymer, the higher the molecular weight necessary to prevent or inhibit leaching.

Forming a Layer

In each of the embodiments, the term "layer" describes a thickness of a polymeric matrix within which an agent must pass through to be released into a subject. This term can refer, for example, to any individual polymeric matrix that may be used to form a medical device or a coating for a medical device. A layer can include, but is not limited to, polymeric material from a single-pass application or multiple-pass application, where a "pass" can be any single process step, or combination of steps, used to apply a material such as, for example, a pass of a spray coating device, a pass of an electrostatic coating device, a pass of a controlled-volume ejector, a dipping, an extrusion, a mold, a single dip in a layered manufacturing process, or a combination thereof. In general, a pass includes any single process step known to one of skill in the art that can be used to apply materials in the formation of a medical device or coating using a composition comprising a polymeric material. A layer can consist of a single pass or multiple passes. In some embodiments, the coating can be applied to an entire medical device or select regions of the medical device.

The term "thickness" can refer to the distance between opposite surfaces of a polymeric matrix that is used in the production of a medical device or coating. The thickness can refer to that of a single layer, a single layer within a combination of layers, or a combination layers.

In some embodiments, the thickness of a polymeric matrix can be the thickness of a component within the structure of a medical device, such as, for example, the thickness of a strut within a stent. In other embodiments, the thickness of a polymeric matrix can be the thickness of a layer of coating applied to a medical device. In other embodiments, the thickness of a polymeric matrix can be the thickness of a combination of layers applied as a coating for a medical device.

In many embodiments, the thickness of a polymeric matrix can range from about 0.1 nm to about 1.0 cm, from about 0.1 nm to about 1.0 mm, from about 0.1 nm to about 100 µm, from about 0.1 nm to about 1 µm, from about 0.1 nm to about 100 nm, from about 0.1 nm to about 10 nm, from about 10 nm to about 100 nm, from about 10 µm to about 50 µm, from about 50 µm to about 100 µm, or any range therein. In other embodiments, the thickness of a polymeric matrix can range from about 1 µm to about 10 µm, which can be found, for example, in some of the current drug-eluting stent (DES) systems. In other embodiments, the thickness of the polymeric matrices can be regionally distributed throughout a device to create a variation in thicknesses such as, for example, the variation in thicknesses that can be found in an abluminally-coated DES stent.

The compositions of the present invention can be in the form of coatings for medical devices such as, for example, a balloon-expandable stent or a self-expanding stent. There are many coating configurations within the scope of the present invention, and each configuration can include any number and combination of layers. In some embodiments, the coatings of the present invention can comprise one or a combination of the following four types of layers:

(a) an agent layer, which may comprise a polymer and an agent or, alternatively, a polymer free agent;
(b) an optional primer layer, which may improve adhesion of subsequent layers on the implantable substrate or on a previously formed layer;
(c) an optional topcoat layer, which may serve as a way of controlling the rate of release of an agent; and
(d) an optional biocompatible finishing layer, which may improve the biocompatibility of the coating.

In many embodiments, each layer can be applied to an implantable substrate by any method including, but not limited to, dipping, spraying, pouring, brushing, spin-coating, roller coating, meniscus coating, powder coating, inkjet-type application, controlled-volume application such as drop-on-demand, or a combination thereof. In these embodiments, a dry coating containing a biodegradable polymer may be formed on the stent when the solvent evaporates. In some embodiments, at least one of the layers can be formed on a stent by dissolving one or more biodegradable polymers, optionally with a non-biodegradable polymer, in one or more solvents, and either (i) spraying the solution on the stent or (ii) dipping the stent in the solution.

In other embodiments, a coating can be applied to a medical device, such as a stent, using methods that may include sputtering and gas-phase polymerization. Sputtering is a method that includes placing a polymeric material target in an environment that is conducive to applying energy to the polymeric material and sputtering the polymeric material from the target to the device to form a coating of the polymeric material on the device. Similarly, a gas-phase polymerization method includes applying energy to a monomer in the gas phase within an environment that is conducive to formation of a polymer from the monomer in the gas phase, and wherein the polymer formed coats the device.

In some embodiments, a pure agent can be applied directly to at least a part of an implantable substrate as a layer to serve as a reservoir for at least one bioactive agent. In another embodiment, the agent can be combined with a polymer. In another embodiment, an optional primer layer can be applied between the implantable substrate and the agent layer to improve adhesion of the agent layer to the implantable substrate and can optionally comprise an agent.

In other embodiments, a pure agent layer can be sandwiched between layers comprising biodegradable polymer.

In other embodiments, the optional topcoat layer can be applied over at least a portion of the agent layer to serve as a topcoat to assist in the control the rate of release of agents and can optionally comprise an agent. In another embodiment, a biocompatible finishing layer can be applied to increase the biocompatibility of the coating by, for example, increasing acute hemocompatibility, and this layer can also comprise an agent.

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures. In some embodiments, the control of the application of energy includes manual control by the operator. In other embodiments, the control of the application of energy includes a programmable heating control system. In some embodiments, the application of energy can result in a coating composition temperature that ranges from about 35° C. to about 100° C., from about 35° C. to about 80° C., from about 35° C. to about 55° C., or any range therein. In some embodiments, any procedure for drying or curing known to one of skill in the art is within the scope of this invention.

In some embodiments, a medical article or coating can also be annealed to enhance the mechanical properties of the composition. Annealing can be used to help reduce part stress and can provide an extra measure of safety in applications such as complex medical devices, where stress-cracking failures can be critical. The annealing can occur at a temperature that ranges from about 30° C. to about 200° C., from about 35° C. to about 190° C., from about 40° C. to about 180° C., from about 45° C. to about 175° C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

The Polymers

A polymeric matrix can comprise polymers that are biodegradable, which can be due to the labile nature of chemical functionalities within the polymer network such as, for example, ester groups that can be present between chemical moieties. Accordingly, these compositions can be designed such that they can be broken down, absorbed, resorbed and eliminated by a mammal. The compositions of the present invention can be used, for example, to form medical articles such as, for example, medical devices and coatings.

The polymers used in the present invention may include, but are not limited to, condensation copolymers, and should be chosen according to a desired performance parameter of a product that will be formed from the composition. Such performance parameters may include, for example, the toughness of a medical device or coating, the capacity for the loading concentration of an agent, and the rate of biodegradation and elimination of the composition from a subject. If the other polymers in a composition are non-biodegradable, they should be sized to produce polymer fragments that can clear from the subject following biodegradation of the composition.

For the purposes of the present invention, a polymer or coating is "biodegradable" when it is capable of being completely or substantially degraded or eroded when exposed to an in vivo environment or a representative in vitro. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation.

In some embodiments, a polymer that is considered biodegradable can be one that has functional groups in its primary backbone that are susceptible to cleavage—usually, but not necessarily, hydrolytic cleavage—when placed in a physiological environment having a primarily aqueous composition. In these embodiments, the environment can have a pH of approximately 7-7.5, one or more hydrolytic enzymes, other endogenous biological compounds that catalyze or at least assist in the degradation process, or a combination thereof. The terms "bioabsorbable" and "biodegradable" can be used interchangeably in some embodiments of this application.

In some embodiments, the number average molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

In some embodiments, the polymers that can be used include natural or synthetic polymers; homopolymers and copolymers, such as, for example, copolymers that are random, alternating, block, graft, and/or crosslinked; or any combination and/or blend thereof. The copolymers include, but are not limited to, polymers with two or more different types of repeating units such as, for example, terpolymers.

In some embodiments, the polymers used in the compositions of the present invention can have a crystallinity at 40° C. that is less than 50 weight percent (wt %), less than less than 30 wt %, less than 20 wt %, or a combination thereof. While not intending to be bound by any theory or mechanism of action, the term "crystallinity" can refer to regions in which polymer chains align with one another, usually parallel, to form crystalline lattices in an effort to obtain the most favorable thermodynamics.

There are a variety of methods used to determine percent crystallinity of a polymer, and each of these methods, although well-known to those skilled in the art, is usually expected to produce a somewhat different crystallinity measurement than may be obtained using a different measurement method for a given polymeric material. While not intending to be bound by any theory or mechanism of action, percent crystallinity can be determined using calorimetry such as, for example thermogravimetric analysis/differential scanning calorimetry; spectroscopy such as, for example, infrared spectroscopy and nuclear magnetic resonance spectroscopy; x-ray diffraction techniques, such as wide-angle x-ray diffraction; gravimetric determinations, including density determinations, specific volume measurements, and the like.

In some embodiments, the polymers include, but are not limited to, poly(acrylates) such as poly(butyl methacrylate), poly(ethyl methacrylate), poly(hydroxylethyl methacrylate), poly(ethyl methacrylate-co-butyl methacrylate), and copolymers of ethylene-methyl methacrylate; poly (2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; and any derivatives, analogs, homologues, congeners, salts, copolymers and combinations thereof.

In some embodiments, the polymers include, but are not limited to, fluorinated polymers or copolymers such as poly (vinylidene fluoride), poly(vinylidene fluoride-co-hexafluoropropene), poly(tetrafluoroethylene), and expanded poly (tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly (hydroxybutyrate-co-valerate); poly(dioxanones); poly (orthoesters); poly(anhydrides); poly(glycolic acid); poly(glycolide); poly(D,L-lactic acid); poly(D,L-lactide); poly (glycolic acid-co-trimethylene carbonate); poly (phosphoesters); poly(phosphoester urethane); poly (trimethylene carbonate); poly(iminocarbonate); poly (ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly (lactic acid); poly(anhydrides), poly(alkylene oxalates); poly (phosphazenes); poly(urethanes); silicones; poly(esters; poly (olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; and any derivatives, analogs, homologues, congeners, salts, copolymers and combinations thereof.

In some embodiments, the polymers include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly (ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, at least one of polymers can be a poly(ester amide), a poly(lactide) or a poly(lactide-co-glycolide) copolymer; and any derivatives, analogs, homologues, congeners, salts, copolymers and combinations thereof. In a variety of embodiments, at least one of the polymers can be a poly(ester amide) and any derivatives, analogs, homologues, congeners, salts, copolymers and combinations thereof. In some embodiments, the polymers are selected such that they specifically exclude any one or any combination of the polymers that are taught herein.

Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof.

In some embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of any of the polymers taught herein.

In some embodiments, the polymers can be chemically connected to agents by covalent bonds. In other embodiments, the polymers can be chemically connected to the agents by non-covalent bonds such as, for example, by ionic bonds, inter-molecular attractions, or a combination thereof. In other embodiments, the polymers can be physically connected to the agents.

In other embodiments, the polymers can be chemically and physically connected with the agents. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed with the agents.

The Agents

Biobeneficial and Bioactive Agents

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly(acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD).

In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents taught herein may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the present invention include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and, any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one embodiment, the bioactive agent inhibits the activity of vascular smooth muscle cells. In another embodiment, the bioactive agent can be used to control migration or proliferation of smooth muscle cells to inhibit restenosis. In another embodiment, the bioactive agent can be used in the prevention and/or treatment of restenosis and/or vulnerable plaque. In some embodiments, the term "treatment" includes, but is not limited to, the mitigation, diagnosis, ameliorization of the symptoms, or a combination thereof, of a disease.

Bioactive agents include, but are not limited to, antiproliferatives, antineoplastics, antimitotics, anti-inflammatories, antiplatelets, anticoagulants, antifibrins, antithrombins, antibiotics, antiallergenics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin $I_1$, actinomycin $X_1$, actinomycin $C_1$, dactinomycin (COSMEGEN®, Merck & Co., Inc.), imatinib mesylate, and any prodrugs, metabolites, analogs, homologues, congeners, derivatives, salts and combinations thereof. Antineoplastics or antimitotics include, for example, paclitaxel (TAXOL®, Bristol-Myers Squibb Co.), docetaxel (TAXOTERE®, Aventis S.A.), midostaurin, methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), midostaurin, and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide; imatinib mesylate; and any prodrugs, metabolites, analogs, homologues, congeners, derivatives, salts and combinations thereof. Antiallergenic agents include, but are not limited to, pemirolast potassium (ALAMAST®, Santen, Inc.), and any prodrugs, metabolites, analogs, homologues, congeners, derivatives, salts and combinations thereof.

Other bioactive agents useful in the present invention include, but are not limited to, free radical scavengers; nitric oxide donors; rapamycin; methyl rapamycin; 42-Epi-(tetrazoylyl)rapamycin (ABT-578); 40-O-(2-hydroxy)ethyl-rapamycin (everolimus); tacrolimus; pimecrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radioopaque materials and include, but are not limited to, materials comprising iodine or iodine-derivatives such as, for example, iohexal and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomography (PET).

Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

Systems for delivering agent combinations can also be used in the present invention and can be more effective at combating restenosis than single drug systems and more efficacious for certain patient subsets such as, for example, patients with diabetes or diffuse, multi-vessel disease. Moreover, combination drugs may be necessary for pro-healing strategies.

In some embodiments, a system for delivery of a combination of agents such as, for example, a combination of clobetasol and everolimus. Clobetasol is a very potent anti-inflammatory drug from a class of drugs called "super potent glucocorticoids." Delivery of clobetasol can inhibit the inflammatory process that can result from, for example, vascular injury incurred through placement of a stent. Vascular injury can release inflammatory cytokines and growth factors that may result in the hyper-proliferation of vascular smooth muscle cells and lead to restenosis. The delivery of clobetasol to the site of injury can inhibit this process. The combination of clobetasol with everolimus can address restenosis on multiple pathways to provide results that may be more beneficial than the results that can be achieved through administration of either drug alone.

In some embodiments, the agent combination includes everolimus and clobetasol. In other embodiments, the agent combination includes tacrolimus and rapamycin. In other embodiments, the agent combination includes tacrolimus and everolimus. In other embodiments, the agent combination can include rapamycin and paclitaxel. In other embodiments, the agent combination can include an anti-inflammatory such as, for example, a corticosteroid and an antiproliferative such as, for example, everolimus. In some embodiments, the agent combinations can provide synergistic effects for preventing or inhibiting conditions such as, for example, restenosis that may occur through use of a stent.

Polycationic peptides such as, for example, hepta-arginine can be dispersed as a dispersed particle phase throughout a polymeric matrix in many forms including, but not limited to, particles resulting from applying coating compositions as emulsions, particles in the form of microspheres, or particles in the form of liposomes. In some embodiments, the peptides can reside in a phase that is separate and dispersed among the polymer phase. The particles can vary in mean diameter from about 1 nm to about 1 cm, from about 1 nm to about 10 mm, from about 1 nm to about 1 mm, from about 1 nm to about 100 nm, or any range therein. In some embodiments, the particles are range from about 0.01 µm to about 5 µm, from about 0.05 µm to about 5 µm, from about 0.10 µm to about 5 µm, from about 0.03 µm to about 0.10 m, or any range therein.

Coating Stents with Polypeptide-Containing Emulsions

In accordance with one embodiment, an emulsion containing a polymer and a polypeptide, for example, hepta-arginine (R7) is prepared. To make the emulsion, R7 can be dissolved in water to form the aqueous phase (solution I). The concentration of R7 in solution I can be between about 5 and 15 mass %. A polymer is then dissolved in a suitable organic solvent, such as dimethylformamide, dimethylsulfoxide, chloroform, methylene chloride, or dimethylacetamide, to form the organic phase (solution II). The concentration of the polymer in solution II can be between about 1 and 15 mass %.

One example of the polymer that can be used for making the organic phase is poly(ethylene-co-vinyl alcohol), the copolymer of ethylene and vinyl alcohol also known under the trade name EVAL and distributed commercially by Aldrich Chemical Company of Milwaukee, Wis. EVAL is also manufactured by EVAL Company of America of Lisle, Ill. EVAL has the general formula $-[CH_2-CH_2]_m-[CH_2-CH(OH)]_n-$. EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers.

Other polymers can be used in lieu of or in addition to EVAL to for preparation of solution II. Examples of such polymers include other vinyl polymers such as poly(vinyl acetate) (PVA), acrylic polymers such as poly(butyl methacrylate) (PBMA) or poly(methyl methacrylate) (PMMA), polyurethanes, and combinations thereof.

The organic phase can also optionally include a surfactant or a mixture of surfactants. The surfactant or the mixture of surfactants can have a hydrophilic-lipophilic balance (HLB) within a range of between about 3 and about 6. Examples of suitable surfactants having HLB between 3 and 6 include SPAN 80 (sorbitan oleate), SPAN 60 (sorbitan monostearates), ARLACEL 83 (sorbitan sesquioleate), TX-4 (polyoxyethylene alkylphenol ether), MOA-3 (polyoxyethylene aliphatic alcohol ether), polyoxamers such as poly(ethylene oxide)-poly(propylene oxide)-poly(ethylene oxide) block-copolymer, egg lechitin, BRIJ 93 (polyoxyethylene oleyl ether), IGEPAL CO-210 (polyoxyethylene nonyl phenyl ether), propylene glycol monostearate, propylene glycol monolaurate, glycerol monolaurate and mixtures thereof.

Surfactants having high HLB (>10) can be also blended with low HLB surfactants described above. Example of suitable high HLB surfactants include TWEEN 20 and TWEEN 21 (polyoxyethylene sorbitan monolaurates), TWEEN 80 (polyoxyethylene sorbitan monooleate), TWEEN 85 (polyoxyethylene sorbitan trioleate), BRIJ 76 and BRIJ 78 (polyoxyethylene stearyl ethers). TWEEN, SPAN, BRIJ, ARLACEL and IGEPAL are trade names of the surfactants. TWEEN, SPAN, BRIJ and ARLACEL are available from ICI Americas, Inc. of Bridgewater, N.J. IGEPAL is available from Rhone-Poulenc, Inc. of Cranbury, N.J.

Solution I is added to solution II and the mixture is sonicated or homogenized to make the water-in-oil emulsion. “Sonication” is defined as agitation by high-frequency sound waves applied to the mixture. The conditions under which the sonication or homogenization is carried out can be determined by one having ordinary skill in the art. The ratio between solution I and solution II can be between about 1:9 and about 1:1 by volume. The R7-containing emulsion can then be applied to a stent by any conventional technique, for example, by spraying or dipping, to form the reservoir matrix of the stent coating. The amount of R7 in this layer can be between about 10 and 200 micrograms.

Optionally, a therapeutic agent or a drug can be incorporated into any coating provided herein such as, for example, by dispersing or dissolving the drug in solution I or II prior to mixing the solutions. The agent could be for inhibiting the activity of vascular smooth muscle cells. It can be directed at inhibiting abnormal or inappropriate migration and/or proliferation of smooth muscle cells to inhibit restenosis. The active agent can include any substance capable of exerting a therapeutic or prophylactic effect in the practice of the present invention. The drug may include small molecule drugs, peptides, proteins, oligonucleotides, or double-stranded DNA. The active agent can also be conjugated to R7 either by covalent attachment or by ionic interaction.

Prior to the application of the reservoir layer, a polymer primer layer can be formed on the bare stent. The polymers for the optional primer layer can be the same polymers that are used to make the reservoir layer.

The coated stent can be optionally freeze-dried to remove the residual solvent and/or moisture. The process of freeze-drying can be carried out using techniques and equipment known to those having ordinary skill in the art. Also, the R7-coated stent can be over-coated with a diffusion limited hydrophobic polymer topcoat if desired. The use of the topcoat is optional. The polymers used for fabrication of the topcoat can include poly(vinylidene fluoride), PBMA, PMMA, or combinations thereof.

Coating Stents with Polymer Compositions Containing Microspheres or Liposomes In accordance with other embodiments, microspheres or liposomes containing a polypeptide, for example R7, can be dispersed in a polymer composition. The polymer composition, containing the microspheres incorporating R7, is then applied to the stent.

In accordance with one embodiment, an encapsulating polymer is dissolved in a suitable organic solvent such as methylene chloride, cyclooctane, cyclohexane, cycloheptane, para-xylene, dimethylformamide, dimethylsulfoxide, chloroform, dimethylacetamide, or mixtures thereof. The encapsulating polymers can include EVAL, other vinyl polymers such as poly(vinyl acetate) (PVA), acrylic polymers such as poly(butyl methacrylate) (PBMA) or poly(methyl methacrylate) (PMMA), polyurethanes, poly(L-lactide), poly(D,L-lactide), poly(glycolide), poly(caprolactone), polyanhydrides, polydiaxanone, polyorthoesters, polyamino acids, poly(trimethylene carbonate), and combinations thereof. The R7 is then added to the polymer solution either as an aqueous solution containing an emulsifying agent such as poly(vinyl alcohol), or as a solid dispersion, and stirred, homogenized or sonicated to create a primary emulsion of R7 in the polymer phase. Surfactants such as poly(vinyl alcohol), albumin (either bovine or human serum), gelatin, lipophilic emulsifiers such as PLURONIC or TETRONIC, or a combination thereof can be optionally added to stabilize the primary emulsion. PLURONIC is a trade name of poly(ethylene oxide-co-propylene oxide). TETRONIC is a trade name of a family of non-ionic tetrafunctional block-copolymer surfactants. PLURONIC and TETRONIC are available from BASF Corp. of Parsippany, N.J.

The primary emulsion is stirred with an aqueous solution containing an emulsifying agent such as poly(vinyl alcohol) to create a secondary emulsion of protein containing polymer in the aqueous phase. The secondary emulsion is stirred in excess water, optionally under vacuum to remove the organic solvent and harden the microspheres. The hardened microspheres are collected by filtration or centrifugation and lyophilized.

According to another technique, a primary emulsion of R7 in an aqueous phase is formed as in the first technique described above. This emulsion is then stirred with a non-solvent for the polymer, such as silicone oil to extract the organic solvent and form embryonic microspheres of polymer with trapped R7. The non-solvent is then removed by the addition of a volatile second non-solvent such as heptane, and the microspheres harden. The hardened microspheres are collected by filtration or centrifugation and lyophilized.

According to yet another technique, the R7, formulated as lyophilized powder is suspended in a polymer phase consisting of polymer dissolved in a volatile organic solvent such as methylene chloride. The suspension is then spray dried to produce polymer microparticles with entrapped R7.

According to yet another technique, the R7, formulated as a powder is suspended in a polymer phase consisting of polymer dissolved in a volatile organic solvent such as methylene chloride. The suspension is sprayed into a container containing frozen ethanol overlaid with liquid nitrogen. The system is then warmed to about −70° C. to liquefy the ethanol and extract the organic solvent from the microspheres. The hardened microspheres are collected by filtration or centrifugation and lyophilized.

Liposomes are aqueous compartment pouches which are typically made of phospholipids. Liposomes can be fabricated according to standard techniques known to those having ordinary skill in the art. One way of forming of the liposome can be by suspending a suitable lipid, such as phosphatidyl choline in an aqueous medium followed by sonication of the mixture. An alternative way of preparing the lipid vesicles can be by rapidly mixing a solution of the lipid in an ethanol-water blend, for example, by injecting the lipid through a needle into a agitated ethanol-water solution. Besides phospholipids, other amphophilic substances can be used, for example, shingomyelin or lipids containing polymerized portions of poly(ethylene glycol). Liposomes having a diameter of about 500 Angstroms can be fabricated.

To trap R7 inside the liposomes, the liposomes can be formed in the presence of R7. For example, in the process of forming the liposomes described above, the aqueous or ethanol-water medium can contain R7. R7 can be dissolved in the medium. For example, if 500 Angstrom vesicles are formed in an approximately decimolar solution of R7 (i.e., the concentration of R7 in the medium is about 0.1 moles per liter), about 2,000 molecules of R7, can be trapped in the inner compartment of each liposome. Following the formation of the R7-filled lipid vesicles, the vesicles can be separated from the surrounding solution and purified, for example, by dialysis or gel-filtration chromatography. Other suitable methods of separation can be employed as is understood by one having ordinary skill in the art.

The R7-containing microspheres or liposomes can then be dispersed in a solution of an appropriate polymer to form a polymer-microsphere or polymer-liposome suspension. The mass ratio between the liposome and the polymer in the suspension can be within a range of between about 1:5 and 1:2. Examples of polymers that can be used, include, but are not limited to, EVAL, other vinyl polymers such as PVA, acrylic polymers such PBMA or PMMA, polyurethanes, and combinations thereof.

The coatings and methods of the present invention are applicable to any implantable medical device. Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (Axius™, Guidant Corp.), vena cava filters, and endocardial leads (Fineline® and Endotak®, Guidant Corp.).

The medical devices can be comprised of a metal or an alloy, including, but not limited to, Elastinite® (Guidant Corp.), Nitinol® (Nitinol Devices and Components), stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (Elgiloy®, Elgiloy Specialty Metals, Inc.; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that are comprised of bioabsorbable polymers or biostable polymers are also included within the scope of the present invention.

In some embodiments, the medical devices described in the present invention comprise a stent. A stent can be used in any part of the vascular system, including neurological, carotid, coronary, renal, aortic, iliac, femoral or any other peripheral vascular sites. The stent can be balloon-expandable, self-expandable and, in many embodiments, the stent can also be biodegradable, such that the stent comprises at least one biodegradable component. There are no limitations on the size of the stent, its length, diameter, strut thickness or pattern. The use of the coating is, however, not limited to stents and the coating can also be used with a variety of other medical devices.

In some embodiments, the stents include, but are not limited to, tubular stents, self-expanding stents, coil stents, ring stents, multi-design stents, and the like. In other embodiments, the stents are metallic; low-ferromagnetic; non-ferromagnetic; biostable polymeric; biodegradable polymeric or biodegradable metallic. In some embodiments, the stents include, but are not limited to, vascular stents, renal stents, biliary stents, pulmonary stents and gastrointestinal stents.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. An implantable medical device comprising a coating, wherein the coating includes a dispersed particle phase comprising a polycationic peptide.

2. The implantable medical device of claim 1, comprising a stent.

3. The implantable medical device of claim 1, wherein the coating comprises a polymer.

4. The implantable medical device of claim 1, wherein the coating comprises a biodegradable polymer.

5. The implantable medical device of claim 2, wherein the stent comprises a biodegradable component.

6. The implantable medical device of claim 1, wherein the coating comprises an acrylic polymer, a vinyl polymer, a polyurethane, or a combination thereof.

7. The implantable medical device of claim 6, wherein the acrylic polymer comprises a component selected from a group consisting of poly(butyl methacrylate) and poly(methyl methacrylate).

8. The implantable medical device of claim 6, wherein the vinyl polymer comprises a component selected from a group consisting of poly(ethylene-co-vinyl alcohol) and poly(vinyl acetate).

9. The implantable medical device of claim 1, wherein the dispersed particle phase comprises a microsphere or liposome.

10. The implantable medical device of claim 9, wherein the microsphere comprises a biodegradable polymer.

11. The implantable medical device of claim 9, wherein the liposome comprises an amphophilic substance.

12. The implantable medical device of claim 11, wherein the amphophilic substance comprises a phospholipid, phosphatidylcholine, shingomyelin, lipids containing polymerized portions of poly(ethylene glycol), or combinations thereof.

13. The implantable medical device of claim 1, wherein the polycationic peptide includes poly(L-arginine), poly(D-arginine), poly(D,L-arginine), a mixture of poly(L-arginine) and poly(D-arginine), poly(L-lysine), poly(D-lysine), poly($\delta$-guanidino-$\alpha$-aminobutyric acid), or mixtures thereof.

14. The implantable medical device of claim 1, wherein the polycationic peptide comprises hepta-arginine.

15. The implantable medical device of claim 1, comprising a diffusion-limiting hydrophobic polymer topcoat.

16. The implantable medical device of claim 1, wherein the coating comprises an agent.

17. The implantable medical device of claim 16, wherein the agent is selected from a group consisting of bioactive agents, biobeneficial agents, diagnostic agents, plasticizing agents, and any prodrugs, codrugs, metabolites, analogs, homologues, congeners, derivatives, salts, and combinations thereof.

18. The implantable medical device of claim 16, wherein the agent is selected from a group consisting of poly(alkylene glycols), phosphorylcholine, poly(N-vinyl pyrrolidone), poly(ethylene oxide), poly(acrylamide methyl propane sulfonic acid), poly(styrene sulfonate), polysaccharides, poly(ester amides), peptides, non-thrombotics, antimicrobials, nitric oxide donors, free radical scavengers, and any prodrugs, codrugs, metabolites, analogs, homologues, congeners, derivatives, salts, and combinations thereof.

19. The implantable medical device of claim 16, wherein the agent is selected from a group consisting of rapamycin, methyl rapamycin, everolimus, pimecrolimus, 42-Epi-(tetrazoylyl)rapamycin (ABT-578), tacrolimus, and any prodrugs, codrugs, metabolites, analogs, homologues, congeners, derivatives, salts, and combinations thereof.

20. The implantable medical device of claim 16, wherein the agent is selected from a group consisting of imatinib mesylate, paclitaxel, docetaxel, midostaurin, and any prodrugs, codrugs, metabolites, analogs, homologues, congeners, derivatives, salts, and combinations thereof.

21. The implantable medical device of claim 16, wherein the agent is selected from a group consisting of estradiol, clobetasol, idoxifen, tazarotene, and any prodrugs, codrugs, metabolites, analogs, homologues, congeners, derivatives, salts, and combinations thereof.

22. The implantable medical device of claim 16, wherein the agent is a combination of agents selected from a group consisting of everolimus and clobetasol; tacrolimus and rapamycin; tacrolimus and everolimus; rapamycin and paclitaxel; and, combinations thereof.

23. The implantable medical device of claim 1, wherein the particle size ranges from about 0.01 μm to about 5 μm in diameter.

24. A method of delivering an agent to a mammalian tissue, wherein the method comprises contacting the stent of claim 2 with the mammalian tissue under in vivo conditions.

25. The method of claim 24, wherein the tissue comprises a vascular tissue.

26. The method of claim 24, wherein the agent comprises hepta-arginine.

27. A method of preventing or treating a disease comprising implanting the stent of claim 2 in a vascular lumen.

28. The method of claim 27, wherein the disease comprises a vascular disease comprising restenosis, vulnerable plaque, or a combination thereof.

29. The method of claim 27, wherein the coating comprises hepta-arginine.

* * * * *